(12) United States Patent
Oh et al.

(10) Patent No.: US 10,889,578 B2
(45) Date of Patent: Jan. 12, 2021

(54) PROCESS FOR PREPARING AMINOPYRIMIDINE DERIVATIVES

(71) Applicant: Yuhan Corporation, Seoul (KR)

(72) Inventors: Sang-Ho Oh, Gyeonggi-do (KR); Ja-Heouk Khoo, Gyeonggi-do (KR); Jong-Chul Lim, Gyeonggi-do (KR); Seong-Ran Lee, Gyeonggi-do (KR); Hyun Ju, Gyeonggi-do (KR); Woo-Seob Shin, Gyeonggi-do (KR); Dae-Gyu Park, Gyeonggi-do (KR); Su-Min Park, Chungcheongbuk-do (KR); Yoon-Ah Hwang, Gyeonggi-do (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 16/633,684

(22) PCT Filed: Jul. 25, 2018

(86) PCT No.: PCT/KR2018/008379
§ 371 (c)(1),
(2) Date: Jan. 24, 2020

(87) PCT Pub. No.: WO2019/022485
PCT Pub. Date: Jan. 31, 2019

(65) Prior Publication Data
US 2020/0165236 A1   May 28, 2020

(30) Foreign Application Priority Data

Jul. 28, 2017 (KR) .................. 10-2017-0096212

(51) Int. Cl.
*C07D 413/14* (2006.01)

(52) U.S. Cl.
CPC .................. *C07D 413/14* (2013.01)

(58) Field of Classification Search
CPC .................................. C07D 413/14
USPC ........................................ 544/106
See application file for complete search history.

(56) References Cited

U.S. PATENT DOCUMENTS

2010/0029610 A1   2/2010 Singh et al.
2016/0102076 A1*  4/2016 Suh .................. A61P 25/00
                                                    514/210.2

FOREIGN PATENT DOCUMENTS

| CN | 104788427 A | 7/2015 |
| WO | 2011/060295 A1 | 5/2011 |
| WO | 2013/014448 A1 | 1/2013 |

* cited by examiner

*Primary Examiner* — Kristin A Vajda
(74) *Attorney, Agent, or Firm* — BakerHostetler

(57) ABSTRACT

The present invention provides an improved process for preparing an aminopyrimidine derivative or pharmaceutically acceptable salt thereof having a selective inhibitory activity against protein kinases, especially against the protein kinases for mutant epidermal growth factor receptors. And also, the present invention provides novel intermediates useful for said process and processes for preparing the same.

33 Claims, No Drawings

PROCESS FOR PREPARING AMINOPYRIMIDINE DERIVATIVES

CROSS-REFERENCE TO RELATED APPLICATIONS

This application is the National Stage of International Patent Application No. PCT/KR2018/008379 filed Jul. 25, 2018, which claims the benefit of Korean application number 10-2017-0096212, filed Jul. 28, 2017, the entire contents of both of which are incorporated herein by reference.

TECHNICAL FIELD

The present invention relates to an improved process for preparing an aminopyrimidine derivative or pharmaceutically acceptable salt thereof. And also, the present invention relates to novel intermediates useful for said process and processes for preparing the same.

BACKGROUND ART

WO 2016/060443 has disclosed an aminopyrimidine derivative or pharmaceutically acceptable salt thereof having a selective inhibitory activity against protein kinases, especially against the protein kinases for mutant epidermal growth factor receptors. Said aminopyrimidine derivative or pharmaceutically acceptable salt thereof can provide an effective and safe therapy against non-small cell lung cancers. WO 2016/060443 has disclosed, as an aminopyrimidine derivative, for example N-(5-(4-(4-((dimethylamino)methyl)-3-phenyl-1H-pyrazol-1-yl)pyrimidin-2-ylamino)-4-methoxy-2-morpholinophenyl)acrylamide of the following Formula 1 and a process for preparing the same.

<Formula 1>

WO 2016/060443 has also disclosed a process for preparing the aminopyrimidine derivative of Formula (I), for example a process according to the following Reaction Scheme. In the following Reaction Scheme, $R_1$ may be methoxy, $R_2$ may be hydrogen, $R_3$ may be morpholinyl, $R_4$ may be hydrogen, $R_5$ may be phenyl, $R_6$ may be hydrogen, and $R_7$ may be dimethylamino.

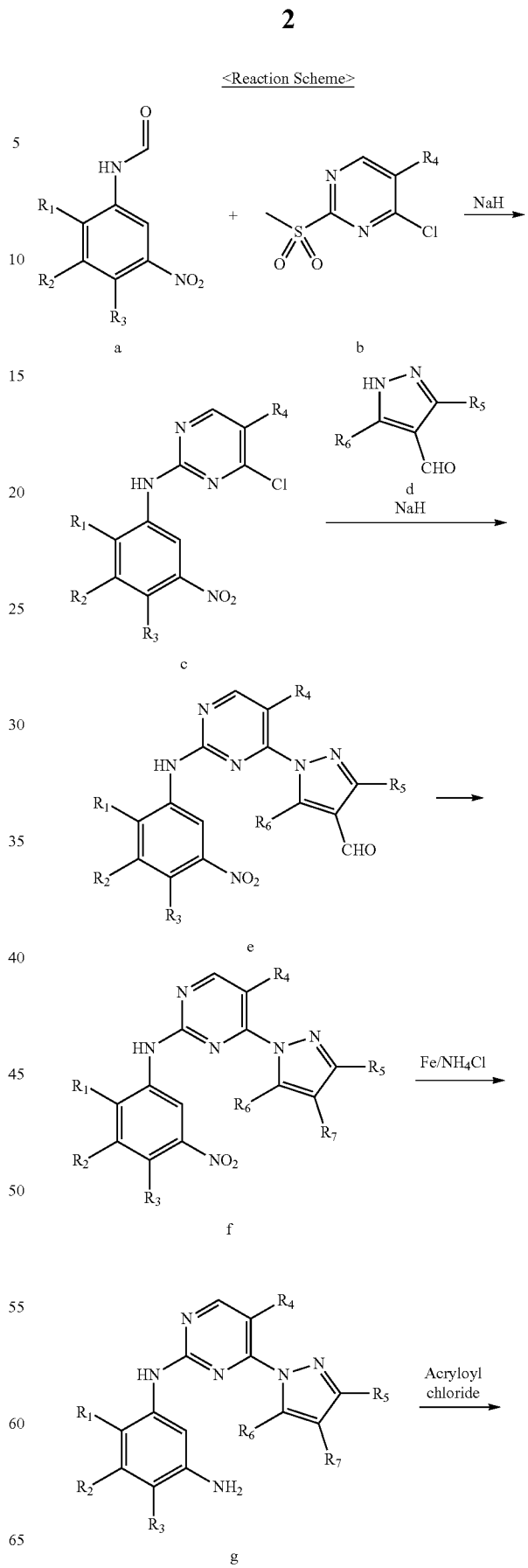

<Reaction Scheme>

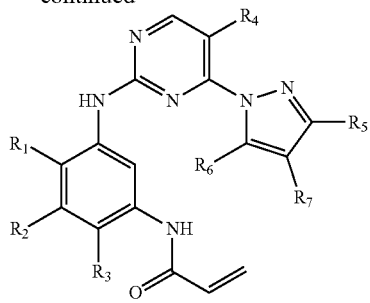

Formula (I)

Specifically, the process for preparing the compound of Formula (I) according to the above Reaction Scheme comprises reacting a compound of Formula (a) with a compound of Formula (b) by use of sodium hydride to obtain a compound of Formula (c); reacting the compound of Formula (c) with a compound of Formula (d) by use of sodium hydride to obtain a compound of Formula (e); performing reductive amination of the compound of Formula (e) to obtain a compound of Formula (f); reducing the compound of Formula (f) by use of iron and ammonium chloride to obtain a compound of Formula (g); and reacting the compound of Formula (g) with acryloyl chloride to obtain a compound of Formula (I).

Said process includes the reactions using sodium hydride, in order to prepare the compound of Formula (c) and the compound of Formula (e). However, since sodium hydride has a high possibility of fire and explosion, there is a problem that it is difficult to use in industrial mass production.

And also, said process includes the use of iron in the step for reducing the nitro group of the compound of Formula (f) to the amino group thereof. However, the use of iron may cause corrosion and contamination in a reactor, which makes it difficult to be applied to mass production. Further, during the reduction using iron and ammonium chloride to obtain the compound of the Formula (g), unknown tars and degradation products are produced; and the product (i.e., the compound of the Formula (g)) is obtained in black color. Therefore, in order to obtain the final product, the compound of formula (I), having a suitable purity, it is required to perform the purification process by column chromatography which is difficult to apply to mass production. In addition, the yield of the step for preparing the compound of Formula (g) is only about 60%.

In addition, since acryloyl chloride used in the final step for preparing the compound of Formula (I) has low stability, it is difficult to handle at the production site. And also, since various degradation products are produced during the reaction of the compound of formula (g) with acryloyl chloride, it is difficult to prepare the compound of Formula (I) having a suitable purity.

DISCLOSURE OF INVENTION

Technical Problem

The present invention provides an improved process which is suitable for industrial mass production and which is able to produce N-(5-(4-(4-((dimethylamino)methyl)-3-phenyl-1H-pyrazol-1-yl)pyrimidin-2-ylamino)-4-methoxy-2-morpholinophenyl)acrylamide (the compound of Formula 1) or a pharmaceutically acceptable salt thereof with high purity and yield.

And also, the present invention provides novel intermediates useful for said process and processes for preparing the same.

Solution to Problem

According to an aspect of the present invention, there is provided a process for preparing N-(5-((4-(4-((dimethylamino)methyl)-3-phenyl-1H-pyrazol-1-yl)pyrimidin-2-yl)amino)-4-methoxy-2-morpholinophenyl)acrylamide (the compound of formula 1) or a pharmaceutically acceptable salt thereof, the process comprising (a) reacting N1-(4-(4-((dimethylamino)methyl)-3-phenyl-1H-pyrazol-1-yl)pyrimidin-2-yl)-6-methoxy-4-morpholinobenzene-1,3-diamine (the compound of Formula 3) with a compound of Formula 4 to obtain a compound of Formula 2; and (b) reacting the compound of Formula 2 with a base to obtain N-(5-((4-(4-((dimethylamino)methyl)-3-phenyl-1H-pyrazol-1-yl)pyrimidin-2-yl)amino)-4-methoxy-2-morpholinophenyl)acrylamide:

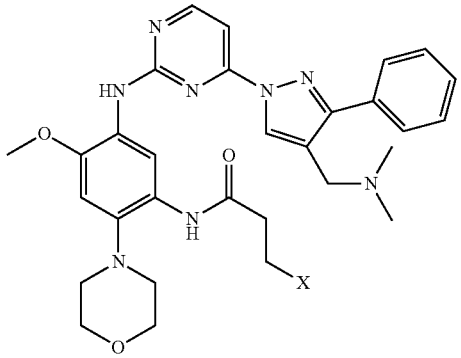

wherein, X is halogen.

In an embodiment, the N1-(4-(4-((dimethylamino)methyl)-3-phenyl-1H-pyrazol-1-yl)pyrimidin-2-yl)-6-methoxy-4-morpholinobenzene-1,3-diamine (the compound of Formula 3) used in Step (a) may be obtained by a process comprising (i) reacting 4-(4-((dimethylamino)methyl)-3-phenyl-1H-pyrazol-1-yl)-N-(2-methoxy-4-morpholino-5-nitrophenyl)pyrimidin-2-amine (the compound of Formula 6) with tin chloride in the presence of hydrochloric acid to obtain a complex of Formula 5 and (ii) reacting the complex of Formula 5 with a base to obtain N1-(4-(4-((dimethylamino)methyl)-3-phenyl-1H-pyrazol-1-yl)pyrimidin-2-yl)-6-methoxy-4-morpholinobenzene-1,3-diamine:

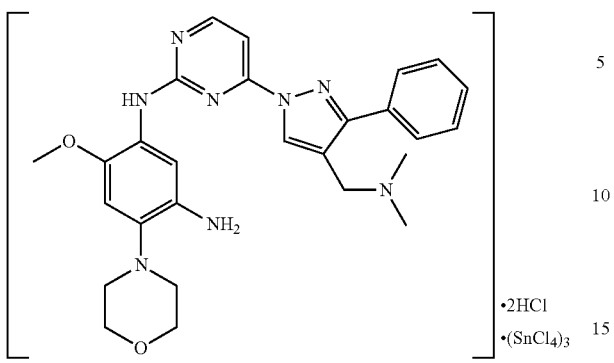

<Formula 5>

In another embodiment, the 4-(4-((dimethylamino)methyl)-3-phenyl-1H-pyrazol-1-yl)-N-(2-methoxy-4-morpholino-5-nitrophenyl)pyrimidin-2-amine (the compound of Formula 6) used in Step (i) may be obtained by reacting 1-(2-((2-methoxy-4-morpholino-5-nitrophenyl)amino)pyrimidin-4-yl)-3-phenyl-1H-pyrazole-4-carbaldehyde (the compound of Formula 7) with dimethylamine or a salt thereof.

In still another embodiment, the 1-(2-((2-methoxy-4-morpholino-5-nitrophenyl)amino)pyrimidin-4-yl)-3-phenyl-1H-pyrazole-4-carbaldehyde (the compound of Formula 7) may be obtained by reacting 4-chloro-N-(2-methoxy-4-morpholino-5-nitrophenyl)pyrimidin-2-amine (the compound of Formula 9) with 3-phenyl-1H-pyrazole-4-carbaldehyde (the compound of Formula 10). The 4-chloro-N-(2-methoxy-4-morpholino-5-nitrophenyl)pyrimidin-2-amine (the compound of Formula 9) may be obtained by reacting N-(2-methoxy-4-morpholino-5-nitrophenyl)formamide (the compound of Formula 11) with 4-chloro-2-(methylsulfonyl)pyrimidine (the compound of Formula 12). And also, the N-(2-methoxy-4-morpholino-5-nitrophenyl)formamide (the compound of Formula 11) may be obtained by performing a formylation of 2-methoxy-4-morpholino-5-nitroaniline (the compound of Formula 13). The 4-chloro-2-(methylsulfonyl)pyrimidine (the compound of Formula 12) may be obtained by performing an oxidation of 4-chloro-2-(methylthio)pyrimidine (the compound of Formula 18). The 2-methoxy-4-morpholino-5-nitroaniline (the compound of Formula 13) may be obtained by reacting 4-fluoro-2-methoxy-5-nitroaniline (the compound of Formula 14) with morpholine (the compound of Formula 15).

In still another embodiment, the 1-(2-((2-methoxy-4-morpholino-5-nitrophenyl)amino)pyrimidin-4-yl)-3-phenyl-1H-pyrazole-4-carbaldehyde (the compound of Formula 7) may be obtained by reacting N-(2-methoxy-4-morpholino-5-nitrophenyl)formamide (the compound of Formula 11) with 1-(2-(methylsulfonyl)pyrimidin-4-yl)-3-phenyl-1H-pyrazole-4-carbaldehyde (the compound of Formula 16). The 1-(2-(methylsulfonyl)pyrimidin-4-yl)-3-phenyl-1H-pyrazole-4-carbaldehyde (the compound of Formula 16) may be obtained by reacting 1-(2-(methylthio)pyrimidin-4-yl)-3-phenyl-1H-pyrazole-4-carbaldehyde (the compound of Formula 17) with an oxidizing agent. The 1-(2-(methylthio)pyrimidin-4-yl)-3-phenyl-1H-pyrazole-4-carbaldehyde (the compound of Formula 17) may be obtained by reacting 4-chloro-2-(methylthio)pyrimidine (the compound of Formula 18) with 3-phenyl-1H-pyrazole-4-carbaldehyde (the compound of Formula 10).

According to another aspect of the present invention, there is provided a compound of Formula 2 or salt thereof:

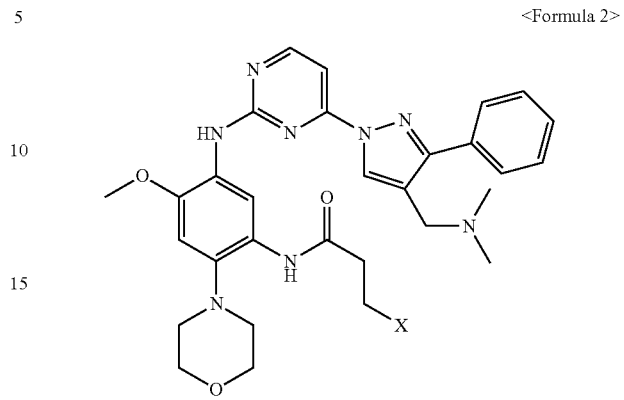

<Formula 2> wherein, X is halogen.

According to still another aspect of the present invention, there is provided a complex of Formula 5:

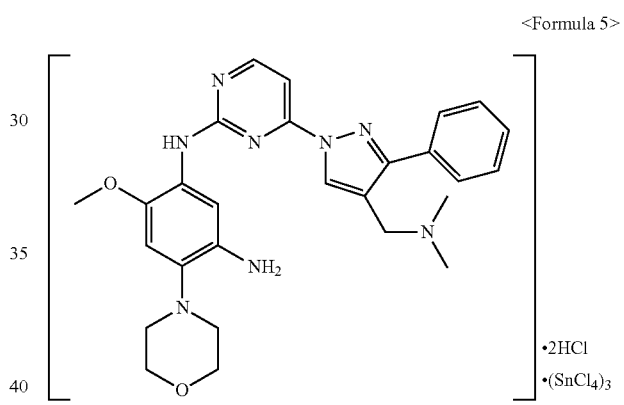

<Formula 5>

According to still another aspect of the present invention, there is provided 1-(2-(methylsulfonyl)pyrimidin-4-yl)-3-phenyl-1H-pyrazole-4-carbaldehyde (the compound of Formula 16).

According to still another aspect of the present invention, there is provided 1-(2-(methylthio)pyrimidin-4-yl)-3-phenyl-1H-pyrazole-4-carbaldehyde (the compound of Formula 17).

Advantageous Effects of Invention

The process of the present invention avoids the use of acryloyl chloride in the step for converting N1-(4-(4-((dimethylamino)methyl)-3-phenyl-1H-pyrazol-1-yl)pyrimidin-2-yl)-6-methoxy-4-morpholinobenzene-1,3-diamine (the compound of Formula 3, i.e., corresponding to the compound of Formula (g) in WO 2016/060443) to N-(5-((4-(4-((dimethylamino)methyl)-3-phenyl-1H-pyrazol-1-yl)pyrimidin-2-yl)amino)-4-methoxy-2-morpholinophenyl)acrylamide (the compound of Formula 1, i.e., corresponding to the compound of Formula (I) in WO 2016/060443). That is, the process of the present invention includes reacting the compound of Formula 3 with 3-halogenopropionyl chloride to obtain a compound of Formula 2 (which is a novel intermediate) and reacting the compound of Formula 2 with a base to obtain the compound of Formula 1, the process of which minimizes the production of degradation products, thereby being able to prepare the compound of Formula 1 in high purity and yield.

And also, the improved process of the present invention may avoid the use of iron and ammonium chloride in the step for converting 4-(4-((dimethylamino)methyl)-3-phenyl-1H-pyrazol-1-yl)-N-(2-methoxy-4-morpholino-5-nitrophenyl)pyrimidin-2-amine (the compound of Formula 6, i.e., corresponding to the compound of Formula (f) in WO 2016/060443) to N1-(4-(4-((dimethylamino)methyl)-3-phenyl-1H-pyrazol-1-yl)pyrimidin-2-yl)-6-methoxy-4-morpholinobenzene-1,3-diamine (the compound of Formula 3, i.e., corresponding to the compound of Formula (g) in WO 2016/060443). That is, the process of the present invention includes reacting the compound of Formula 6 with tin chloride in the presence of an acid to obtain a complex of the compound of Formula 6 and tin chloride; and reacting the complex with a base to obtain the compound of Formula 3, the process of which makes it possible to prepare the compound of Formula 3 in high yield (e.g., 75% or more) and in high purity. And also, said process is able to solve the problems of corrosion and contamination in a reactor which is caused by the use of iron. In addition, said process can avoid the production of unknown tars and degradation products; and therefore avoid performing the purification process by column chromatography unsuitable for industrial mass production.

In addition, the improved process of the present invention is able to exclude the use of sodium hydride having a high possibility of fire and explosion in the steps for preparing the key intermediates, i.e., 4-chloro-N-(2-methoxy-4-morpholino-5-nitrophenyl)pyrimidin-2-amine (the compound of Formula 9, i.e., corresponding to the compound of Formula (c) in WO 2016/060443) and 1-(2-((2-methoxy-4-morpholino-5-nitrophenyl)amino)pyrimidin-4-yl)-3-phenyl-1H-pyrazole-4-carbaldehyde (the compound of Formula 7, i.e., corresponding to the compound of Formula (e) in WO 2016/060443). Therefore, the process of the present invention is suitable for industrial mass production.

BEST MODE FOR CARRYING OUT THE INVENTION

The present invention provides an improved process for preparing N-(5-((4-(4-((dimethylamino)methyl)-3-phenyl-1H-pyrazol-1-yl)pyrimidin-2-yl)amino)-4-methoxy-2-morpholinophenyl)acrylamide or a pharmaceutically acceptable salt thereof. The overall reaction schemes of the process of the present invention are represented as the following Reaction Scheme 1 or 2.

<Reactin Scheme 1>

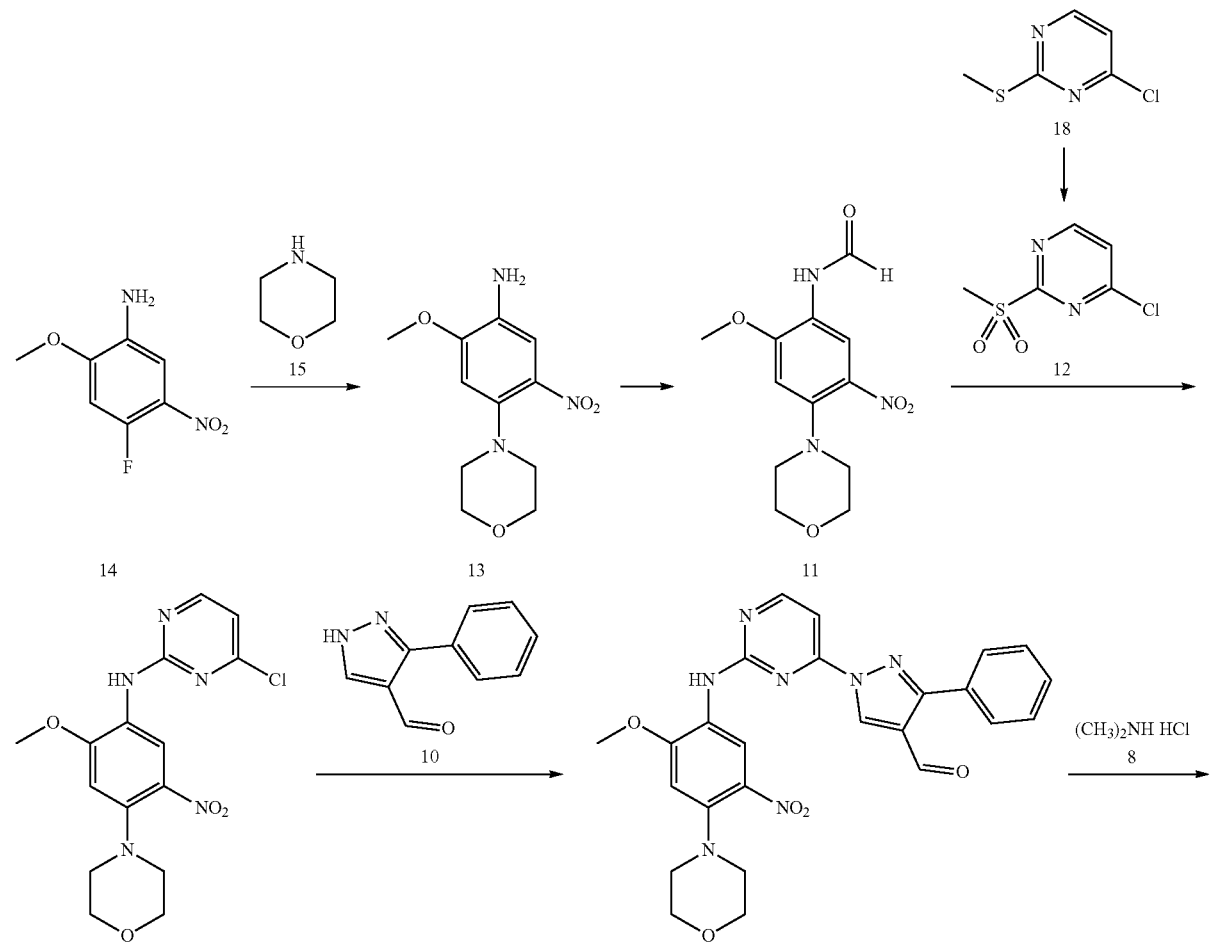

-continued
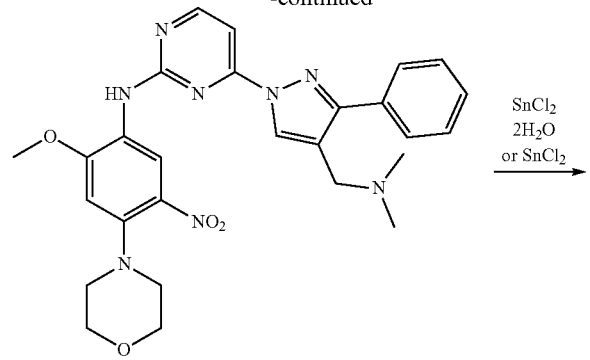
6
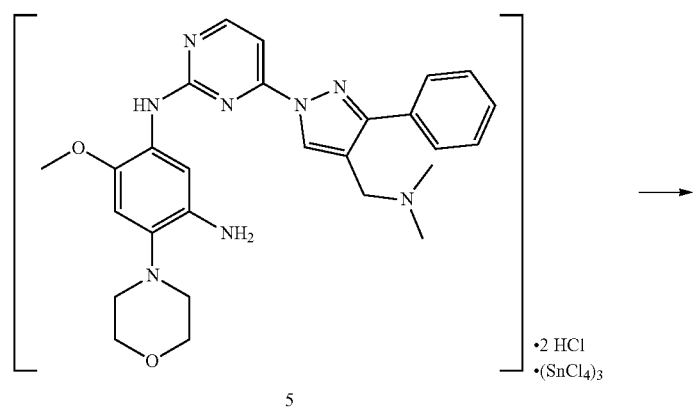
5
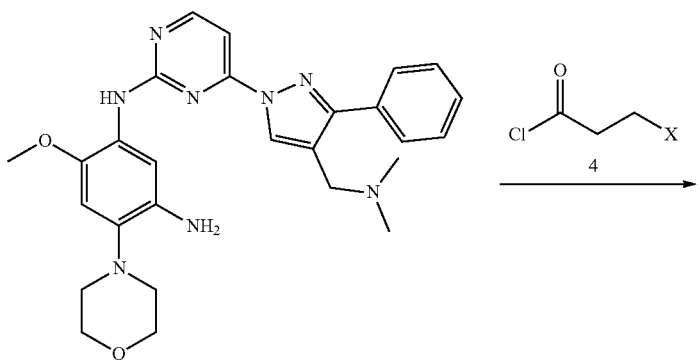
3
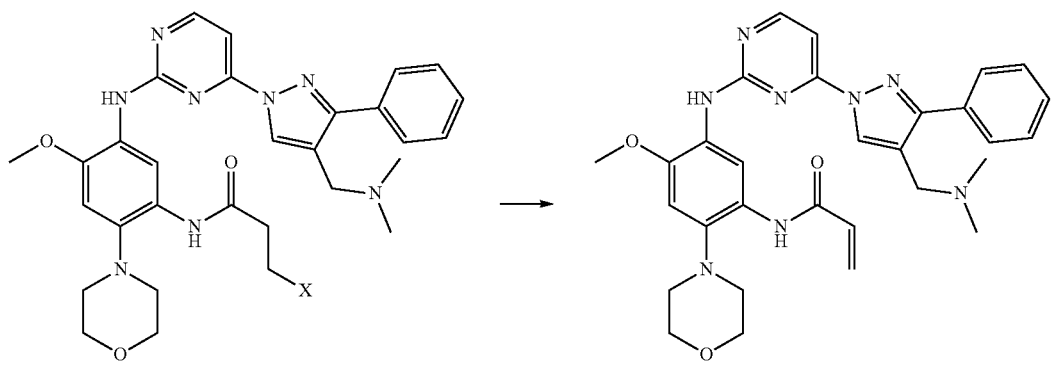

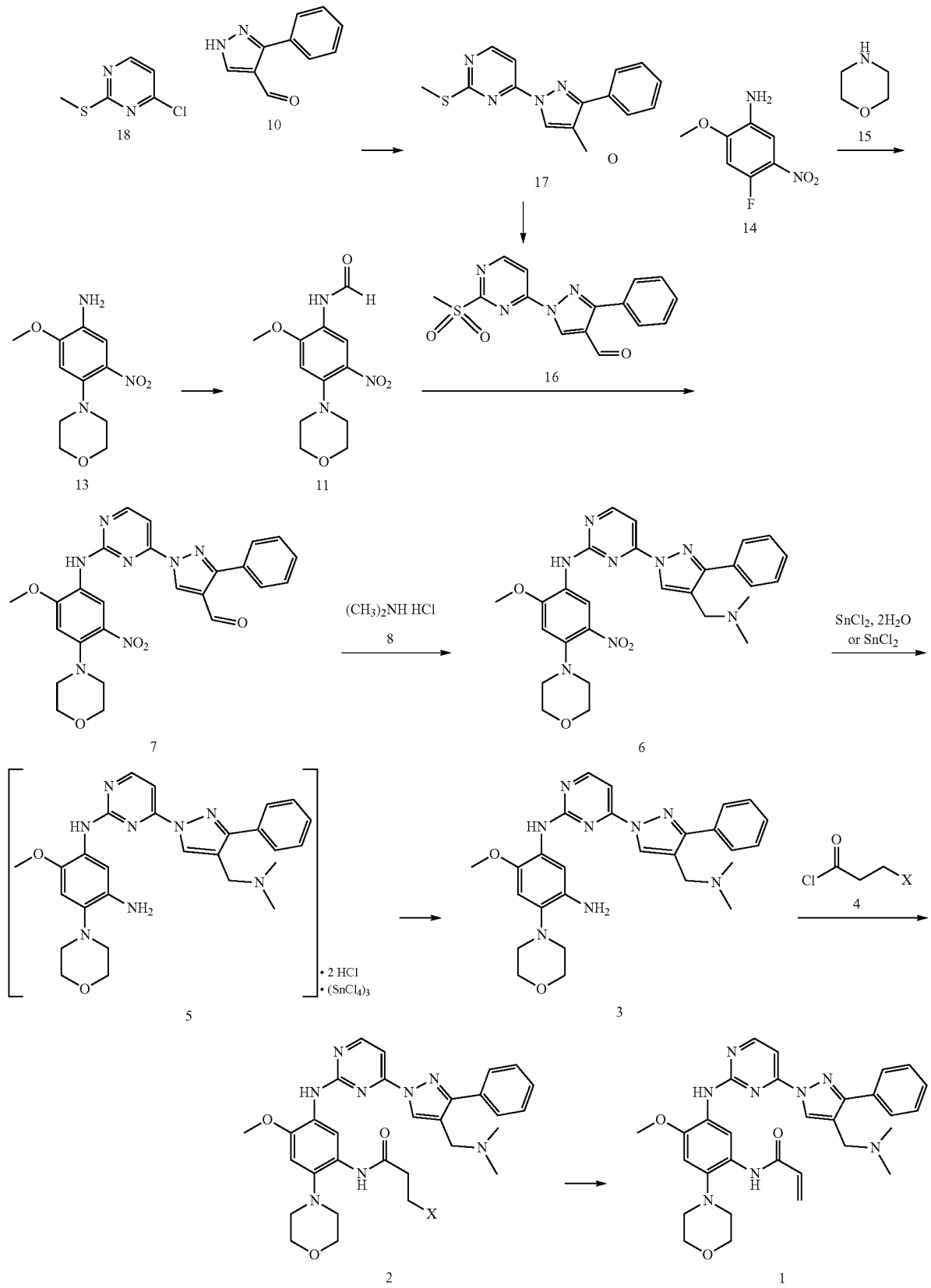
<Reaction Scheme 2>

Hereinafter, the process of the present invention will be described in detail with reference to the respective steps of the Reaction Schemes 1 and 2.

The present invention provides a process for preparing N-(5-((4-(4-((dimethylamino)methyl)-3-phenyl-1H-pyrazol-1-yl)pyrimidin-2-yl)amino)-4-methoxy-2-morpholinophenyl)acrylamide (the compound of formula 1) or a pharmaceutically acceptable salt thereof, the process comprising (a) reacting N1-(4-(4-((dimethylamino)methyl)-3-phenyl-1H-pyrazol-1-yl)pyrimidin-2-yl)-6-methoxy-4-morpholinobenzene-1,3-diamine (the compound of Formula 3) with a compound of Formula 4 to obtain a compound of Formula 2; and (b) reacting the compound of Formula 2 with a base to obtain N-(5-((4-(4-((dimethylamino)methyl)-3-phenyl-1H-pyrazol-1-yl)pyrimidin-2-yl)amino)-4-methoxy-2-morpholinophenyl)acrylamide:

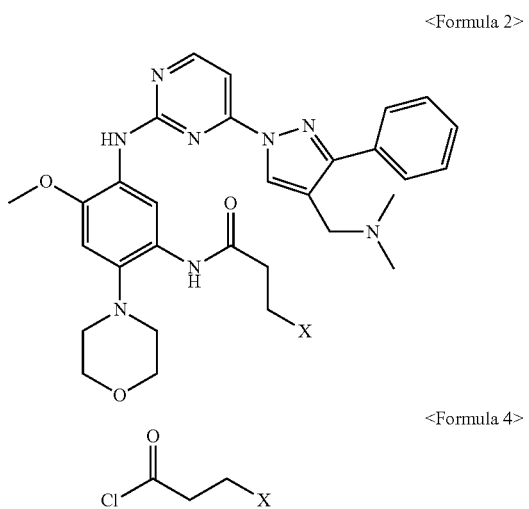

<Formula 2>

<Formula 4> wherein, X is halogen.

In the process of the present invention, X is preferably chlorine or bromine.

In the process of the present invention, the reacting of Step (a) may be carried out in the presence of one or more base(s) selected from the group consisting of potassium tert-butoxide, sodium hydroxide, potassium hydroxide, lithium hydroxide, sodium hydride, sodium carbonate, sodium bicarbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. Preferably, the base may be sodium bicarbonate. The base may be used in an amount ranging from 1.0 to 5.0 equivalents, preferably from 1.0 to 3.0 equivalents, per 1 equivalent of the compound of Formula 3. The reacting of Step (a) may be carried out in the presence of a solvent selected from the group consisting of acetonitrile, methyl ethyl ketone, acetone, methyl isobutyl ketone, dichloromethane, dichloroethane, dimethylformamide, dimethylacetamide, dimethyl sulfoxide, tetrahydrofuran, $C_1$~$C_5$ alcohol, toluene, ethyl acetate, isopropyl acetate, diethyl ether, water and a mixture thereof. Preferably, the solvent may be selected from the group consisting of acetonitrile, tetrahydrofuran, methyl ethyl ketone, acetone, dichloromethane, water and a mixture thereof. More preferably, the solvent may be a mixed solvent of acetonitrile and water, a mixed solvent of methyl ethyl ketone and water or a mixed solvent of tetrahydrofuran and water. The reaction of the compound of Formula 3 with the compound of Formula 4 may be carried out at a temperature ranging from 0 to 50° C., preferably from 0 to 30° C. The compound of Formula 2 may be isolated according to conventional methods, such as concentration (e.g., concentration under reduced pressure etc.), filtration, drying, and so on.

The base used in Step (b) may be one or more selected from the group consisting of potassium tert-butoxide, sodium hydroxide, potassium hydroxide, lithium hydroxide, sodium hydride, sodium carbonate, sodium bicarbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. Preferably, the base may be one or more selected from the group consisting of sodium hydroxide, triethylamine and diisopropylamine. More preferably, the base may be triethylamine. The base may be used in an amount ranging from 1.0 to 20.0 equivalents, preferably from 5.0 to 10.0 equivalents, per 1 equivalent of the compound of Formula 2. The reacting of Step (b) may be carried out in the presence of a solvent selected from the group consisting of acetonitrile, methyl ethyl ketone, acetone, methyl isobutyl ketone, dichloromethane, dichloroethane, dimethylformamide, dimethylacetamide, dimethyl sulfoxide, tetrahydrofuran, $C_1$~$C_5$ alcohol, toluene, ethyl acetate, isopropyl acetate, diethyl ether, water and a mixture thereof. Preferably, the solvent may be selected from the group consisting of acetonitrile, tetrahydrofuran, methyl ethyl ketone, acetone, dichloromethane, water and a mixture thereof. More preferably, the solvent may be a mixed solvent of acetonitrile and water, a mixed solvent of methyl ethyl ketone and water or a mixed solvent of tetrahydrofuran and water. The reaction of the compound of Formula 2 with the base may be carried out at a temperature ranging from 40 to 150° C., preferably at a temperature ranging from 60 to 100° C., more preferably at the reflux temperature of the used solvent. The compound of Formula 1 prepared from said reaction may be isolated in the form of free base or in the form of organic or inorganic salt (for example, in the form of mesylate salt) according to conventional methods.

In an embodiment of the process of the present invention, Step (a) and Step (b) may be carried out in a one-pot reaction, without isolating the compound of Formula 2. Therefore, the process of the present invention is suitable for industrial mass production.

In the process of the present invention, the N1-(4-(4-((dimethylamino)methyl)-3-phenyl-1H-pyrazol-1-yl)pyrimidin-2-yl)-6-methoxy-4-morpholinobenzene-1,3-diamine (the compound of Formula 3) used in Step (a) may be obtained by a process comprising (i) reacting 4-(4-((dimethylamino)methyl)-3-phenyl-1H-pyrazol-1-yl)-N-(2-methoxy-4-morpholino-5-nitrophenyl)pyrimidin-2-amine (the compound of Formula 6) with tin chloride in the presence of hydrochloric acid to obtain a complex of Formula 5 and (ii) reacting the complex of Formula 5 with a base to obtain N1-(4-(4-((dimethylamino)methyl)-3-phenyl-1H-pyrazol-1-yl)pyrimidin-2-yl)-6-methoxy-4-morpholinobenzene-1,3-diamine:

<Formula 5>

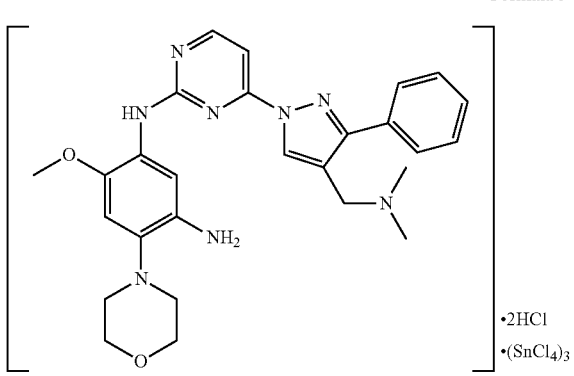

·2HCl
·(SnCl₄)₃

In Step (i), said tin chloride may be used in the form of anhydrate or hydrate (e.g., dihydrate). The tin chloride may be used in an amount ranging from 2.0 to 10.0 equivalents, preferably from 3.0 to 5.0 equivalents, per 1 equivalent of the compound of Formula 6. The acid may be used in an amount ranging from 2.0 to 10.0 equivalents per 1 equivalent of the compound of Formula 6. And also, the reacting of Step (i) may be carried out at a temperature ranging from 0 to 100° C., preferably from 40 to 85° C. Therefore, the reaction may be carried out under a mild condition; and thus is suitable for industrial mass production. The reaction may be carried out in the presence of one or more solvent(s) selected from the group consisting of water, $C_1$~$C_{10}$ alcohol (for example, methanol, ethanol, propanol, isopropanol, butanol, and so on), dichloromethane, tetrahydrofuran, acetonitrile and ethyl acetate. In an embodiment, the solvent may be ethanol or a mixed solvent of ethanol and dichloromethane. The complex of Formula 5 produced from Step (i) may be subject to the subsequent step [i.e., Step (ii)], without the isolation thereof. And also, the complex of Formula 5 produced from Step (i) may be isolated from the reaction mixture per se or isolated by crystallization with an antisolvent. The antisolvent may be one or more selected from the group consisting of dichloromethane, ethyl acetate, $C_1$~$C_5$ alcohol (for example, methanol, ethanol, isopropanol, butanol, and so on), acetone, acetonitrile, methyl ethyl ketone, tetrahydrofuran, hexamethylphosphoramide, dimethyl ether, diethyl ether, diisopropyl ether, ethyl acetate, dimethoxyethane and toluene. Preferably, the antisolvent may be dichloromethane. Although the amount of the antisolvent to be used is not particularly limited, the antisolvent may be used in a weight ratio ranging from 2 to 20 times, preferably from 3 to 10 times, based on the complex of Formula 5. The crystallization may be also carried out at a temperature ranging from 0 to 40° C., preferably from 0 to 25° C.

Step (ii) provides the N1-(4-(4-((dimethylamino)methyl)-3-phenyl-1H-pyrazol-1-yl)pyrimidin-2-yl)-6-methoxy-4-morpholinobenzene-1,3-diamine (the compound of Formula 3) through reacting the complex of Formula 5 with a base. The base may be one or more selected from the group consisting of sodium hydroxide, potassium hydroxide, sodium carbonate, sodium bicarbonate, potassium carbonate, potassium phosphate (including potassium phosphate monobasic, potassium phosphate dibasic, and potassium phosphate tribasic), and sodium phosphate (including sodium phosphate monobasic, sodium phosphate dibasic and sodium phosphate tribasic). Preferably, the base may be sodium hydroxide.

In the process of the present invention, the 4-(4-((dimethylamino)methyl)-3-phenyl-1H-pyrazol-1-yl)-N-(2-methoxy-4-morpholino-5-nitrophenyl)pyrimidin-2-amine (the compound of Formula 6) used in Step (i) may be obtained by reacting 1-(2-((2-methoxy-4-morpholino-5-nitrophenyl)amino)pyrimidin-4-yl)-3-phenyl-1H-pyrazole-4-carbaldehyde (the compound of Formula 7) with dimethylamine or a salt thereof. The reacting may be carried out in the presence of one or more reducing agent(s) selected from the group consisting of sodium triacetoxyborohydride, sodium cyanoborohydride and sodium borohydride, preferably the presence of sodium triacetoxyborohydride. The reducing agent may be used in an amount ranging from 1.0 to 5.0 equivalents, preferably from 1.0 to 2.0 equivalents, per 1 equivalent of the compound of Formula 7, although the amount thereof may vary according to the reducing agents. The reacting may be carried out in the presence of one or more base(s) selected from the group consisting of diisopropylethylamine and triethylamine. And also, the reacting may be carried out in the presence of one or more solvent(s) selected from the group consisting of $C_1$~$C_{10}$ alcohol (for example, methanol, ethanol, propanol, isopropanol, butanol, and so on), dimethylacetamide, dimethylformamide, dichloromethane, tetrahydrofuran, acetonitrile and ethyl acetate. The reacting may be carried out at a temperature ranging from 0 to 50° C., preferably from 20 to 30° C. Therefore, the reaction may be carried out under a mild condition; and thus is suitable for industrial mass production. The compound of Formula 6 produced from said reaction may be isolated from the reaction mixture per se or isolated by crystallization with an antisolvent. The antisolvent may be $C_1$~$C_5$ alcohol (for example, methanol, ethanol, isopropanol, butanol, and so on), water, or a mixture thereof, preferably water. Although the amount of the antisolvent to be used is not particularly limited, the antisolvent may be used in a weight ratio ranging from 2 to 20 times, preferably from 3 to 10 times, based on the complex of Formula 7. The crystallization may be also carried out at a temperature ranging from 0 to 40° C., preferably from 20 to 30° C.

In an embodiment, the 1-(2-((2-methoxy-4-morpholino-5-nitrophenyl)amino)pyrimidin-4-yl)-3-phenyl-1H-pyrazole-4-carbaldehyde (the compound of Formula 7) may be obtained by reacting 4-chloro-N-(2-methoxy-4-morpholino-5-nitrophenyl)pyrimidin-2-amine (the compound of Formula 9) with 3-phenyl-1H-pyrazole-4-carbaldehyde (the compound of Formula 10) (see Reaction Scheme 1). The reaction of the compound of Formula 9 with the compound of Formula 10 may be carried out in the presence of one or more base(s) selected from the group consisting of potassium tert-butoxide, sodium hydroxide, potassium hydroxide, sodium hydride, sodium carbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. Preferably, the base may be one or more selected from the group consisting of sodium carbonate, potassium carbonate, and potassium phosphate. And also, the reaction may be carried out in the presence of one or more solvent(s) selected from the group consisting of dichloromethane, dichloroethane, dimethylformamide, dimethylacetamide, dimethyl sulfoxide, tetrahydrofuran, $C_1$~$C_5$ alcohol, ethyl acetate, acetone, methyl ethyl ketone, acetonitrile and toluene. Preferably, the solvent may be selected from the group consisting of dichloromethane, dimethylformamide and dimethylacetamide. More preferably, the solvent may be dimethylformamide. And also, the reaction may be carried out at a temperature ranging from 0 to 100° C., preferably from 40 to 60° C.

In the process of the present invention, the 4-chloro-N-(2-methoxy-4-morpholino-5-nitrophenyl)pyrimidin-2-amine (the compound of Formula 9) may be obtained by reacting N-(2-methoxy-4-morpholino-5-nitrophenyl)formamide (the compound of Formula 11) with 4-chloro-2-(methylsulfonyl)pyrimidine (the compound of Formula 12) (see Reaction Scheme 1). The reaction of the compound of Formula 11 with the compound of Formula 12 may be carried out in the presence of one or more base(s) selected from the group consisting of sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine and triethylamine. Preferably, the base may be sodium $C_1$~$C_6$ alkoxide or potassium $C_1$~$C_6$ alkoxide. And also, the reaction may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be dimethylformamide, dimethylacetamide, tetrahydrofuran, or a mixture thereof. And also, the reaction may be carried out at a temperature ranging from 0 to 50° C., preferably from 0 to 10° C.

In the process of the present invention, the N-(2-methoxy-4-morpholino-5-nitrophenyl)formamide (the compound of Formula 11) may be obtained by performing a formylation of 2-methoxy-4-morpholino-5-nitroaniline (the compound of Formula 13) (see Reaction Scheme 1). The formylation may be carried out with a mixture of acetic acid (e.g., anhydrous acetic acid) and formic acid. Each amount of acetic acid and formic acid to be used may range from 2 to 5 moles, preferably from 2.5 to 3.5 moles, per 1 mole of the compound of Formula 13. And also, the formylation may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be dimethylformamide, dimethylacetamide, tetrahydrofuran, or a mixture thereof. And also, the reaction may be carried out at a temperature ranging from 0 to 70° C., preferably from 20 to 50° C.

In the process of the present invention, the 4-chloro-2-(methylsulfonyl)pyrimidine (the compound of Formula 12) may be obtained by performing an oxidation of 4-chloro-2-(methylthio)pyrimidine (the compound of Formula 18). The oxidation may be carried out with one or more oxidizing agent(s) selected from the group consisting of potassium permanganate, chromic acid, oxygen, hydrogen peroxide and 3-chloroperbenzoic acid. Preferably, the oxidizing agent may be hydrogen peroxide. The amount of the oxidizing agent to be used may range from 1.8 to 10.0 moles, preferably from 2.0 to 5.0 moles, per 1 mole of the compound of Formula 18. And also, the reaction rate can be increased by performing the oxidation in the presence of a catalyst such as ammonium molybdate tetrahydrate. In addition, the reaction may be carried out in the presence of one or more solvent(s) selected from the group consisting of $C_1$~$C_5$ alcohol, carbon tetrachloride, chloroform, dichloromethane, acetone, methyl ethyl ketone, methyl isobutyl ketone, cyclohexanone, pentane, hexane, heptane, octane, nonane, decane, undecane, dodecane, cyclohexane, petroleum ether, kerosene, toluene, xylene, mesitylene and benzene. Preferably, the solvent may be $C_1$~$C_5$ alcohol.

In the process of the present invention, the 2-methoxy-4-morpholino-5-nitroaniline (the compound of Formula 13) may be obtained by reacting 4-fluoro-2-methoxy-5-nitroaniline (the compound of Formula 14) with morpholine (the compound of Formula 15). The reaction may be carried out in the presence of one or more base(s) selected from the group consisting of sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine, triethylamine and diisopropylethylamine. Preferably, the base may be triethylamine or diisopropylethylamine. The reaction may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be selected from the group consisting of acetonitrile, dimethylformamide and dimethylacetamide. And also, the reaction may be carried out at a temperature ranging from 0 to 100° C., preferably from 70 to 80° C.

In another embodiment, the 1-(2-((2-methoxy-4-morpholino-5-nitrophenyl)amino)pyrimidin-4-yl)-3-phenyl-1H-pyrazole-4-carbaldehyde (the compound of Formula 7) may be obtained by reacting N-(2-methoxy-4-morpholino-5-nitrophenyl)formamide (the compound of Formula 11) with 1-(2-(methylsulfonyl)pyrimidin-4-yl)-3-phenyl-1H-pyrazole-4-carbaldehyde (the compound of Formula 16) (see Reaction Scheme 2). The reaction of the compound of Formula 11 with the compound of Formula 16 may be carried out in the presence of one or more base(s) selected from the group consisting of sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine, and triethylamine. Preferably, the base may be one or more selected from the group consisting of sodium $C_1$~$C_6$ alkoxide, potassium $C_1$~$C_6$ alkoxide, sodium carbonate, potassium carbonate, and potassium phosphate. If the compound of Formula 7 is prepared according to the Reaction Scheme 2, it is possible to avoid the use of sodium hydride. And also, the reaction may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be dimethylformamide, dimethylacetamide, tetrahydrofuran, or a mixture thereof. And also, the reaction may be carried out at a temperature ranging from 0 to 50° C., preferably from 0 to 10° C.

In the process of the present invention, the 1-(2-(methylsulfonyl)pyrimidin-4-yl)-3-phenyl-1H-pyrazole-4-carbaldehyde (the compound of Formula 16) may be obtained by reacting 1-(2-(methylthio)pyrimidin-4-yl)-3-phenyl-1H-pyrazole-4-carbaldehyde (the compound of Formula 17) with an oxidizing agent (see Reaction Scheme 2). The oxidation may be carried out with one or more oxidizing agent(s) selected from the group consisting of potassium permanganate, chromic acid, oxygen, hydrogen peroxide and 3-chloroperbenzoic acid. Preferably, the oxidizing agent may be hydrogen peroxide. The amount of the oxidizing agent to be used may range from 1.8 to 10.0 moles, preferably from 2.0 to 5.0 moles, per 1 mole of the compound of Formula 17. And also, the reaction rate can be increased by performing the oxidation in the presence of a catalyst such as ammonium molybdate tetrahydrate. In addition, the reaction may be carried out in the presence of one or more solvent(s) selected from the group consisting of $C_1$-$C_5$ alcohol, carbon tetrachloride, chloroform, dichloromethane, acetone, methyl ethyl ketone, methyl isobutyl ketone, cyclohexanone, pentane, hexane, heptane, octane, nonane, decane, undecane, dodecane, cyclohexane, petroleum ether, kerosene, toluene, xylene, mesitylene and benzene.

In the process of the present invention, the 1-(2-(methylthio)pyrimidin-4-yl)-3-phenyl-1H-pyrazole-4-carbaldehyde (the compound of Formula 17) may be obtained by reacting 4-chloro-2-(methylthio)pyrimidine (the compound of Formula 18) with 3-phenyl-1H-pyrazole-4-carbaldehyde (the compound of Formula 10). The reaction of the compound of Formula 18 with the compound of Formula 10 may be carried out in the presence of one or more base(s) selected from the group consisting of potassium tert-butoxide, sodium hydroxide, potassium hydroxide, sodium hydride, sodium carbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. Preferably, the base may be selected from the group consisting of sodium carbonate, potassium carbonate, and potassium phosphate. The reaction may be carried out in the presence of one or more solvent(s) selected from the group consisting of dichloromethane, dichloroethane, dimethylformamide, dimethylacetamide, dimethyl sulfoxide, tetrahydrofuran, $C_1$-$C_5$ alcohol, ethyl acetate, acetone, methyl ethyl ketone, acetonitrile and toluene. Preferably, the solvent may be selected from the group consisting of dichloromethane, dimethylformamide and dimethylacetamide. More preferably, the solvent may be dimethylformamide. And also, the reaction may be carried out at a temperature ranging from 0 to 100° C., preferably from 40 to 60° C.

The present invention includes, within its scope, novel intermediates useful for said improved processes.

That is, the present invention provides a compound of Formula 2 or salt thereof:

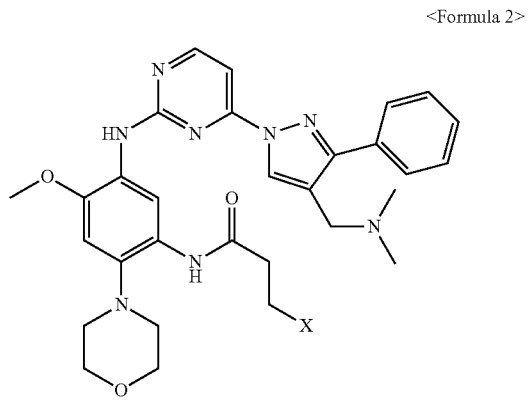

<Formula 2> wherein, X is halogen.

And also, the present invention provides a complex of Formula 5:

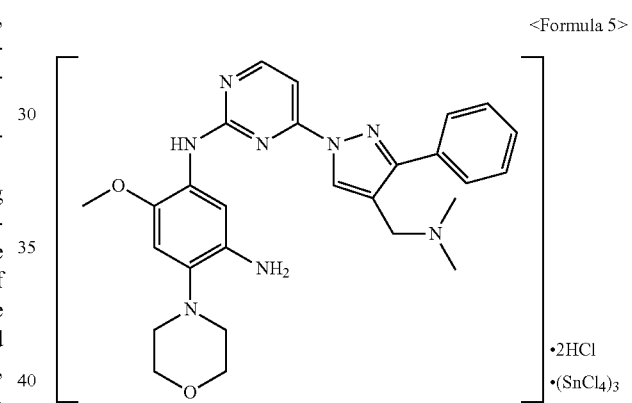

<Formula 5>

·2HCl
·(SnCl$_4$)$_3$

And also, the present invention provides 1-(2-(methylsulfonyl)pyrimidin-4-yl)-3-phenyl-1H-pyrazole-4-carbaldehyde (the compound of Formula 16).

And also, the present invention provides 1-(2-(methylthio)pyrimidin-4-yl)-3-phenyl-1H-pyrazole-4-carbaldehyde (the compound of Formula 17).

The following examples are provided for illustration purposes only, and are not intended to limit the scope of the invention.

Example 1. Preparation of
2-methoxy-4-morpholino-5-nitroaniline (Compound 13)

A mixture of 4-fluoro-2-methoxy-5-nitroaniline (60.0 g, 0.322 mol), acetonitrile (600.0 mL), diisopropylethylamine (83.3 g, 0.645 mol), and morpholine (84.2 g, 0.967 mol) was refluxed under stirring for 4 hours. To the reaction mixture, was purified water (1.8 L) added. The resulting solid was filtered and then dried in vacuo to obtain 78.0 g of the titled compound. (Yield: 95.5%)

$^1$H-NMR (400 MHz, DMSO) δ 7.21 (s, 1H), 6.76 (s, 1H), 5.03 (s, 2H), 3.89 (s, 3H), 3.69 (t, 4H), 2.92 (t, 4H)

Example 2. Preparation of N-(2-methoxy-4-morpholino-5-nitrophenyl)formamide (Compound 11)

A mixture of anhydrous acetic acid (254.0 g, 2.487 mol) and formic acid (137.4 g, 2.984 mol) was stirred at 50° C. for 30 minutes. 2-Methoxy-4-morpholino-5-nitroaniline (210.0 g, 0.829 mol) and tetrahydrofuran (219.0 mL) were added to the reaction mixture, which was then stirred at 20-25° C. for 1 hour. To the reaction mixture, was methyl tert-butyl ether (2.1 L) added. The resulting solid was filtered and then dried in vacuo to obtain 211.0 g of the titled compound. (Yield: 90.5%)

$^1$H-NMR (400 MHz, DMSO) δ 9.88 (s, 1H), 8.85 (s, 1H), 8.29 (d, 1H), 6.83 (s, 1H), 3.99 (s, 1H), 3.72-3.74 (t, 4H), 3.03-3.05 (t, 4H)

Example 3. Preparation of 4-chloro-2-(methylsulfonyl)pyrimidine (Compound 12)

A 35% hydrogen peroxide solution (90.7 g, 0.933 mol) and ammonium molybdate tetrahydrate (11.5 g, 0.01 mol) were added to a solution of 4-chloro-2-(methylthio)pyrimidine (50.0 g, 0.311 mol) in ethanol (250.0 mL). The reaction mixture was stirred for 2 hours and then extracted with dichloromethane (200.0 mL) and purified water (250.0 mL). The separated organic layer was washed with a 10% sodium sulfite solution and purified water and then concentrated under reduced pressure. The resulting residue was crystallized by adding isopropyl alcohol thereto. The resulting solid was filtered and then dried in vacuo to obtain 51.2 g of the titled compound. (Yield: 85.4%)

$^1$H-NMR (400 MHz, DMSO) δ 9.05 (d, 1H), 8.06 (d, 1H), 3.42 (s, 3H)

Example 4. Preparation of 4-chloro-N-(2-methoxy-4-morpholino-5-nitrophenyl)pyrimidin-2-amine (Compound 9)

A mixture of N-(2-methoxy-4-morpholino-5-nitrophenyl)formamide (15.0 g, 0.05 mol), tetrahydrofuran (40.0 mL), and dimethylacetamide (60.0 mL) was cooled to 0-5° C. Sodium tert-butoxide (5.6 g, 0.06 mol) and 4-chloro-2-(methylsulfonyl)pyrimidine (11.3 g, 0.06 mol) were added to the mixture, which was then stirred at 0-10° C. for 1 hour. A 2N NaOH solution (75.0 mL) was added to the reaction mixture. The reaction mixture was stirred at room temperature for 1 hour and then purified water (150.0 mL) was added thereto. The resulting solid was filtered and then dried in vacuo to obtain 16.1 g of the titled compound. (Yield: 82.6%)

$^1$H-NMR (400 MHz, DMSO) δ 8.94 (s, 1H), 8.38-8.40 (t, 2H), 6.95 (d, 1H), 6.83 (s, 1H), 6.95 (d, 1H), 6.83 (s, 1H), 3.94 (s, 3H), 3.73-3.75 (t, 4H), 3.06-3.08 (t, 4H)

Example 5. Preparation of 1-(2-(methylthio)pyrimidin-4-yl)-3-phenyl-1H-pyrazole-4-carbaldehyde (Compound 17)

A mixture of 4-chloro-2-(methylthio)pyrimidine (102.6 g, 0.639 mol), 3-phenyl-1H-pyrazole-4-carbaldehyde (100.0 g, 0.581 mol), potassium carbonate (160.5 g, 1.162 mol), and dimethylformamide (700.0 mL) was stirred at 40-50° C. for 2 hours. Purified water (1.6 L) was slowly added to the reaction mixture, which was then stirred at room temperature for 2 hours. The resulting solid was filtered and then dried in vacuo to obtain 154.0 g of the titled compound. (Yield: 81.4%)

$^1$H-NMR (400 MHz, CDCl$_3$) δ 10.10 (s, 1H), 9.20 (s, 1H), 8.65 (d, 1H), 7.84-7.86 (m, 2H), 7.67-7.71 (m, 3H), 2.65 (s, 3H)

Example 6. Preparation of 1-(2-(methylsulfonyl)pyrimidin-4-yl)-3-phenyl-1H-pyrazole-4-carbaldehyde (Compound 16)

A 35% hydrogen peroxide solution (3.4 g, 30.3 mmol) and ammonium molybdate tetrahydrate (0.4 g, 0.3 mmol) were added to a solution of 1-(2-(methylthio)pyrimidin-4-yl)-3-phenyl-1H-pyrazole-4-carbaldehyde (3.0 g, 10.1 mmol) in ethanol (21.0 mL). The reaction mixture was stirred for 2 hours and then extracted with dichloromethane (30.0 mL) and purified water (30.0 mL). The separated organic layer was washed with a 10% sodium sulfite solution (21.0 mL) and purified water and then concentrated under reduced pressure. The resulting residue was crystallized by adding isopropyl alcohol thereto. The resulting solid was filtered and then dried in vacuo to obtain 2.8 g of the titled compound. (Yield: 84.3%)

$^1$H-NMR (400 MHz, CDCl$_3$) δ 10.12 (s, 1H), 9.30 (s, 1H), 9.00 (d, 1H), 8.27 (d, 2H), 7.87-7.93 (m, 2H), 7.48-7.54 (m, 3H), 3.44 (s, 3H)

Example 7. Preparation of 1-(2-((2-methoxy-4-morpholino-5-nitrophenyl)amino)pyrimidin-4-yl)-3-phenyl-1H-pyrazole-4-carbaldehyde (Compound 7)

A mixture of 4-chloro-N-(2-methoxy-4-morpholino-5-nitrophenyl)pyrimidin-2-amine (3.2 g, 0.009 mol), dimethylformamide (22.4 mL), potassium carbonate (2.4 g, 0.017 mol), and 3-phenyl-1H-pyrazole-4-carbaldehyde (1.7 g, 0.010 mol) was stirred at 40-50° C. for 12 hours. To the reaction mixture, was purified water (32.0 mL) added. The resulting solid was filtered and then dried in vacuo to obtain 4.3 g of the titled compound. (Yield: 98.0%)

$^1$H-NMR (400 MHz, DMSO) 8.94 (s, 1H), 8.38 (d, 1H), 8.38 (s, 1H), 6.96 (d, 1H), 6.83 (s, 1H), 3.94 (s, 3H), 3.73-3.75 (t, 4H), 3.06-3.09 (t, 4H)

Example 8. Preparation of 1-(2-((2-methoxy-4-morpholino-5-nitrophenyl)amino)pyrimidin-4-yl)-3-phenyl-1H-pyrazole-4-carbaldehyde (Compound 7)

A mixture of N-(2-methoxy-4-morpholino-5-nitrophenyl)formamide (0.4 g, 1.4 mmol), tetrahydrofuran (2.6 mL), dimethylacetamide (1.8 mL) and sodium tert-butoxide (0.2 g, 2.0 mmol) was stirred at 10° C. for 2 hours. After the temperature of the reaction mixture was adjusted to room temperature, 1-(2-(methylsulfonyl)pyrimidin-4-yl)-3-phenyl-1H-pyrazole-4-carbaldehyde (0.5 g, 1.5 mmol) was added thereto. The reaction mixture was stirred at room temperature for 1 hour. A 2N NaOH solution (2.1 mL) was added to the reaction mixture, which was then stirred for about 1 hour. The resulting solid was filtered and then dried in vacuo to obtain 0.67 g of the titled compound. (Yield: 93.9%)

$^1$H-NMR (400 MHz, DMSO) 8.94 (s, 1H), 8.38 (d, 1H), 8.38 (s, 1H), 6.96 (d, 1H), 6.83 (s, 1H), 3.94 (s, 3H), 3.73-3.75 (t, 4H), 3.06-3.09 (t, 4H)

Example 9. Preparation of 4-(4-((dimethylamino) methyl)-3-phenyl-1H-pyrazol-1-yl)-N-(2-methoxy-4-morpholino-5-nitrophenyl)pyrimidin-2-amine (Compound 6)

Dimethylamine hydrochloride (39.0 g, 0.479 mol) and triethylamine (161.4 g, 1.595 mol) were added to a solution of 1-(2-((2-methoxy-4-morpholino-5-nitrophenyl)amino) pyrimidin-4-yl)-3-phenyl-1H-pyrazole-4-carbaldehyde (160.0 g, 0.319 mol) in dimethylformamide (1,120 mL). The reaction mixture was stirred at room temperature for 30 minutes. Sodium triacetoxyborohydride (121.7 g, 0.574 mol) was added to the reaction mixture, which was then stirred at room temperature for 3 hours. Purified water (2,240 mL) was added to the reaction mixture, which was then stirred for 1 hour. The resulting solid was filtered under reduced pressure and then dried in vacuo to obtain 164.0 g of the titled compound. (Yield: 96.9%)

$^1$H-NMR (400 MHz, DMSO) δ 8.92 (s, 1H), 8.57-8.61 (q, 3H), 7.98 (d, 2H), 7.52 (d, 2H), 7.50 (s, 1H), 7.36 (s, 1H), 6.88 (s, 1H), 4.01 (s, 3H), 3.75-3.77 (t, 4H), 3.41 (s, 2H), 3.07-3.10 (t, 4H), 2.24 (s, 6H)

Example 10. Preparation of N1-(4-(4-((dimethylamino)methyl)-3-phenyl-1H-pyrazol-1-yl)pyrimidin-2-yl)-6-methoxy-4-morpholinobenzene-1,3-diamine tin complex (Compound 5)

A mixture of 4-(4-((dimethylamino)methyl)-3-phenyl-1H-pyrazol-1-yl)-N-(2-methoxy-4-morpholino-5-nitrophenyl)pyrimidin-2-amine (10 g, 0.019 mol), tin chloride dihydrate (21.3 g, 0.094 mol), ethanol (200.0 mL), and a 35% hydrochloric acid solution (13.1 mL, 0.151 mol) was refluxed under stirring for 2 hours. The reaction mixture was cooled to 20-30° C. Dichloromethane (100.0 mL) was slowly added to the reaction mixture, which was then stirred for 2 hours. The resulting solid was filtered under reduced pressure and then dried in vacuo to obtain 21.6 g of the titled compound.

$^1$H-NMR (400 MHz, DMSO) δ 10.07 (br, 1H), 10.01 (br, 1H), 9.24 (s, 1H), 8.62-8.63 (d, 1H), 8.55 (s, 1H), 8.18 (s, 1H), 7.73-7.74 (d, 2H), 7.51-7.58 (m, 3H), 7.39-7.40 (d, 1H), 7.13 (s, 1H), 4.54 (s, 2H), 3.92 (s, 3H), 3.81 (s, 4H), 2.91 (s, 4H), 2.70 (s, 6H)

Example 11. Preparation of N1-(4-(4-((dimethylamino)methyl)-3-phenyl-1H-pyrazol-1-yl)pyrimidin-2-yl)-6-methoxy-4-morpholinobenzene-1,3-diamine tin complex (Compound 5)

A mixture of 4-(4-((dimethylamino)methyl)-3-phenyl-1H-pyrazol-1-yl)-N-(2-methoxy-4-morpholino-5-nitrophenyl)pyrimidin-2-amine (20 g, 0.038 mol), ethanol (400.0 mL), dichloromethane (200.0 mL), and a 35% hydrochloric acid solution (26.2 mL, 0.302 mol) was stirred for 30 minutes. Tin chloride dihydrate (42.5 g, 0.189 mol) was added to the reaction mixture, which was then refluxed under stirring for 2 hours. The reaction mixture was cooled to room temperature and then stirred for 2 hours. The resulting solid was filtered under reduced pressure and then dried in vacuo to obtain 40.6 g of the titled compound. (Content Yield: 82.1%)

$^1$H-NMR (400 MHz, DMSO) δ 10.07 (br, 1H), 10.01 (br, 1H), 9.24 (s, 1H), 8.62-8.63 (d, 1H), 8.55 (s, 1H), 8.18 (s, 1H), 7.73-7.74 (d, 2H), 7.51-7.58 (m, 3H), 7.39-7.40 (d, 1H), 7.13 (s, 1H), 4.54 (s, 2H), 3.92 (s, 3H), 3.81 (s, 4H), 2.91 (s, 4H), 2.70 (s, 6H)

Example 12. Preparation of N1-(4-(4-((dimethylamino)methyl)-3-phenyl-1H-pyrazol-1-yl)pyrimidin-2-yl)-6-methoxy-4-morpholinobenzene-1,3-diamine (Compound 3)

A mixture of N1-(4-(4-((dimethylamino)methyl)-3-phenyl-1H-pyrazol-1-yl)pyrimidin-2-yl)-6-methoxy-4-morpholinobenzene-1,3-diamine tin complex (40.6 g), dichloromethane (200.0 mL), and a 2N NaOH solution (200.0 mL) was stirred at room temperature for 1 hour and then filtered. After the resulting filtrate was left standing, the separated organic layer was treated with activated carbon and then concentrated under reduced pressure. Ethanol (100.0 mL) was added to the mixture, which was then stirred. The resulting solid was filtered and then dried in vacuo to obtain 14.2 g of the titled compound. (Yield: 75.2%)

$^1$H-NMR (400 MHz, DMSO) δ 8.57 (s, 1H), 8.48 (d, 1H), 8.16 (s, 1H), 7.95 (d, 2H), 7.41-7.49 (m, 4H), 7.28 (s, 1H), 6.72 (s, 1H), 4.53 (s, 2H), 3.75-3.77 (t, 7H), 3.42 (s, 2H), 2.83 (t, 3H), 2.22 (s, 6H)

Example 13. Preparation of 3-chloro-N-(5-((4-(4-((dimethylamino)methyl)-3-phenyl-1H-pyrazol-1-yl) pyrimidin-2-yl)amino)-4-methoxy-2-morpholinophenyl)propanamide (Compound 2, X=Cl)

3-Chloropropionyl chloride (0.16 g, 1.30 mmol) was added to a mixture of N1-(4-(4-((dimethylamino)methyl)-3-phenyl-1H-pyrazol-1-yl)pyrimidin-2-yl)-6-methoxy-4-morpholinobenzene-1,3-diamine (0.5 g, 0.99 mmol), sodium bicarbonate (0.25 g, 2.99 mmol), and acetonitrile (5.0 mL). The reaction mixture was stirred at 20-30° C. for 3 hours. Purified water (5.0 mL) was added to the reaction mixture, which was stirred for 1 hour and then filtered under reduced pressure. The resulting solid was dried in vacuo to obtain 0.50 g of the titled compound. (Yield: 85.0%)

$^1$H-NMR (400 MHz, DMSO) δ 9.09 (s, 1H), 9.06 (s, 1H), 8.79 (s, 1H), 8.50-8.51 (d, 1H), 8.17 (s, 1H), 8.02 (d, 2H), 7.45-7.48 (t, 2H), 7.39-7.42 (t, 1H), 7.31 (d, 1H), 6.89 (s, 1H), 3.98-3.99 (t, 2H), 3.88 (s, 3H), 3.78-3.80 (t, 4H), 3.43 (s, 2H), 2.85-2.86 (t, 4H), 2.21 (s, 6H)

Example 14. Preparation of 3-bromo-N-(5-((4-(4-((dimethylamino)methyl)-3-phenyl-1H-pyrazol-1-yl) pyrimidin-2-yl)amino)-4-methoxy-2-morpholinophenyl)propanamide (Compound 2, X=Br)

3-Bromopropionyl chloride (0.13 mL, 1.297 mmol) was slowly added to a mixture of N1-(4-(4-((dimethylamino) methyl)-3-phenyl-1H-pyrazol-1-yl)pyrimidin-2-yl)-6-methoxy-4-morpholinobenzene-1,3-diamine (0.5 g, 0.998 mmol), sodium bicarbonate (0.25 g, 3.00 mmol), and acetonitrile (5.0 mL). The reaction mixture was stirred at 20-30° C. for 3 hours. Purified water (5.0 mL) was added to the reaction mixture, which was stirred for 1 hour and then filtered under reduced pressure. The resulting solid was dried in vacuo to obtain 0.52 g of the titled compound. (Yield: 81.9%)

$^1$H-NMR (400 MHz, DMSO) δ 9.08 (s, 2H), 8.80 (s, 1H), 8.50 (d, 1H), 8.16 (s, 1H), 8.02 (d, 2H), 7.45-7.48 (t, 2H), 7.39-7.42 (t, 1H), 7.31 (s, 1H), 3.88 (s, 3H), 3.83-3.85 (t, 2H), 3.79-3.81 (t, 4H), 3.43 (s, 2H), 3.09-3.12 (t, 2H), 2.85-2.87 (t, 4H), 2.19 (s, 6H)

Example 15. Preparation of N-(5-((4-(4-((dimethylamino)methyl)-3-phenyl-1H-pyrazol-1-yl)pyrimidin-2-yl)amino)-4-methoxy-2-morpholinophenyl)acrylamide (Compound 1)

A mixture of 3-bromo-N-(5-((4-(4-((dimethylamino) methyl)-3-phenyl-1H-pyrazol-1-yl)pyrimidin-2-yl)amino)-

4-methoxy-2-morpholinophenyl)propanamide (10.0 g, 16.9 mmol), acetonitrile (200.0 mL), and triethylamine (17.1 g, 169.2 mmol) was refluxed under stirring for 16 hours. The reaction mixture was cooled to 20-30° C. and then concentrated under reduced pressure to remove the solvent. Dichloromethane (100.0 mL) and purified water (100.0 mL) were added to the reaction mixture, which was then stirred. The separated organic layer was concentrated under reduced pressure and then n-propanol (200.0 mL) was added thereto, followed by refluxing under stirring. The reaction mixture was slowly cooled to 20-30° C. and then stirred for 2 hours. The resulting solid was filtered under reduced pressure and then dried in vacuo to obtain 8.0 g of the titled compound. (Yield: 85.0%)

$^1$H-NMR (400 MHz, DMSO) δ 9.15 (s, 2H), 9.08 (s, 1H), 8.53-8.55 (d, 1H), 8.18 (s, 1H), 8.04-8.06 (d, 2H), 7.47-7.50 (m. 2H), 7.34-7.36 (m, 1H), 7.34 (d, 1H), 6.96 (s, 1H), 6.71-6.78 (q, 1H), 6.43-6.44 (d, 1H), 5.84-5.85 (d, 1H), 3.91 (s, 3H), 3.82 (s, 4H), 3.46 (1 s, 1H), 2.86 (s, 4H), 2.21 (s, 6H)

Example 16. Preparation of N-(5-((4-(4-((dimethylamino)methyl)-3-phenyl-1H-pyrazol-1-yl)pyrimidin-2-yl)amino)-4-methoxy-2-morpholinophenyl)acrylamide (Compound 1)

3-Chloropropionyl chloride (0.3 g, 2.60 mmol) was added to a mixture of N1-(4-(4-((dimethylamino)methyl)-3-phenyl-1H-pyrazol-1-yl)pyrimidin-2-yl)-6-methoxy-4-morpholinobenzene-1,3-diamine (1.0 g, 1.99 mmol), acetonitrile (20.0 mL), and sodium bicarbonate (0.5 g, 5.99 mmol). The reaction mixture was stirred at 20-30° C. for 2 hours. Triethylamine (2.0 g, 19.9 mmol) was added to the reaction mixture, which was then refluxed under stirring for 16 hours. The reaction mixture was cooled to 20-30° C. and then concentrated under reduced pressure to remove the solvent. Dichloromethane (15.0 mL) and purified water (10.0 mL) were added to the reaction mixture, which was then stirred. The separated organic layer was concentrated under reduced pressure and then n-propanol (20.0 mL) was added thereto, followed by refluxing under stirring. The reaction mixture was slowly cooled to 20-30° C. and then stirred for 2 hours. The resulting solid was filtered under reduced pressure and then dried in vacuo to obtain 0.83 g of the titled compound. (Yield: 75.0%)

$^1$H-NMR (400 MHz, DMSO) δ 9.15 (s, 2H), 9.08 (s, 1H), 8.53-8.55 (d, 1H), 8.18 (s, 1H), 8.04-8.06 (d, 2H), 7.47-7.50 (m. 2H), 7.34-7.36 (m, 1H), 7.34 (d, 1H), 6.96 (s, 1H), 6.71-6.78 (q, 1H), 6.43-6.44 (d, 1H), 5.84-5.85 (d, 1H), 3.91 (s, 3H), 3.82 (s, 4H), 3.46 (1 s, 1H), 2.86 (s, 4H), 2.21 (s, 6H)

Example 17. Preparation of N-(5-((4-(4-((dimethylamino)methyl)-3-phenyl-1H-pyrazol-1-yl)pyrimidin-2-yl)amino)-4-methoxy-2-morpholinophenyl)acrylamide (Compound 1)

3-Chloropropionyl chloride (0.3 g, 2.60 mmol) was added to a mixture of N1-(4-(4-((dimethylamino)methyl)-3-phenyl-1H-pyrazol-1-yl)pyrimidin-2-yl)-6-methoxy-4-morpholinobenzene-1,3-diamine (1.0 g, 1.99 mmol), tetrahydrofuran (17.0 mL), purified water (1.7 mL), and sodium bicarbonate (1.1 g, 5.99 mmol). The reaction mixture was stirred at 20-30° C. for 2 hours. Triethylamine (2.0 g, 19.9 mmol) was added to the reaction mixture, which was then refluxed under stirring for 16 hours. The reaction mixture was cooled to 20-30° C. and then concentrated under reduced pressure to remove the solvent. Dichloromethane (10.0 mL) and purified water (10.0 mL) were added to the reaction mixture, which was then stirred. The separated organic layer was concentrated under reduced pressure and then n-propanol (20.0 mL) was added thereto, followed by refluxing under stirring. The reaction mixture was slowly cooled to 20-30° C. and then stirred for 2 hours. The resulting solid was filtered under reduced pressure and then dried in vacuo to obtain 0.88 g of the titled compound. (Yield: 79.5%)

$^1$H-NMR (400 MHz, DMSO) δ 9.15 (s, 2H), 9.08 (s, 1H), 8.53-8.55 (d, 1H), 8.18 (s, 1H), 8.04-8.06 (d, 2H), 7.47-7.50 (m. 2H), 7.34-7.36 (m, 1H), 7.34 (d, 1H), 6.96 (s, 1H), 6.71-6.78 (q, 1H), 6.43-6.44 (d, 1H), 5.84-5.85 (d, 1H), 3.91 (s, 3H), 3.82 (s, 4H), 3.46 (1 s, 1H), 2.86 (s, 4H), 2.21 (s, 6H)

Example 18. Preparation of N-(5-((4-(4-((dimethylamino)methyl)-3-phenyl-1H-pyrazol-1-yl)pyrimidin-2-yl)amino)-4-methoxy-2-morpholinophenyl)acrylamide (Compound 1)

3-Chloropropionyl chloride (6.6 g, 0.052 mol) was added to a mixture of N1-(4-(4-((dimethylamino)methyl)-3-phenyl-1H-pyrazol-1-yl)pyrimidin-2-yl)-6-methoxy-4-morpholinobenzene-1,3-diamine (20.0 g, 0.039 mol), methyl ethyl ketone (160.0 mL), and sodium bicarbonate (10.1 g, 0.120 mol). The reaction mixture was stirred at 20-30° C. for 2 hours. Dichloromethane (10.0 mL) and purified water (10.0 mL) were added to the reaction mixture, which was then stirred. The separated organic layer was concentrated under reduced pressure and then methyl ethyl ketone (300.0 mL) and triethylamine (40.4 g, 0.400 mol) were added thereto, followed by refluxing under stirring for 10 hours. The reaction mixture was cooled to 0-5° C. and then stirred for 2 hours. The resulting solid was filtered under reduced pressure and then dried in vacuo to obtain 17.7 g of the titled compound. (Yield: 79.9%)

$^1$H-NMR (400 MHz, DMSO) δ 9.15 (s, 2H), 9.08 (s, 1H), 8.53-8.55 (d, 1H), 8.18 (s, 1H), 8.04-8.06 (d, 2H), 7.47-7.50 (m. 2H), 7.34-7.36 (m, 1H), 7.34 (d, 1H), 6.96 (s, 1H), 6.71-6.78 (q, 1H), 6.43-6.44 (d, 1H), 5.84-5.85 (d, 1H), 3.91 (s, 3H), 3.82 (s, 4H), 3.46 (1 s, 1H), 2.86 (s, 4H), 2.21 (s, 6H)

The invention claimed is:

1. A process for preparing N-(5-((4-(4-((dimethylamino)methyl)-3-phenyl-1H-pyrazol-1-yl)pyrimidin-2-yl)amino)-4-methoxy-2-morpholinophenyl)acrylamide or a pharmaceutically acceptable salt thereof, the process comprising (a) reacting N1-(4-(4-((dimethylamino)methyl)-3-phenyl-1H-pyrazol-1-yl)pyrimidin-2-yl)-6-methoxy-4-morpholinobenzene-1,3-diamine with a compound of Formula 4 to obtain a compound of Formula 2; and (b) reacting the compound of Formula 2 with a base to obtain N-(5-((4-(4-((dimethylamino)methyl)-3-phenyl-1H-pyrazol-1-yl)pyrimidin-2-yl)amino)-4-methoxy-2-morpholinophenyl)acrylamide:

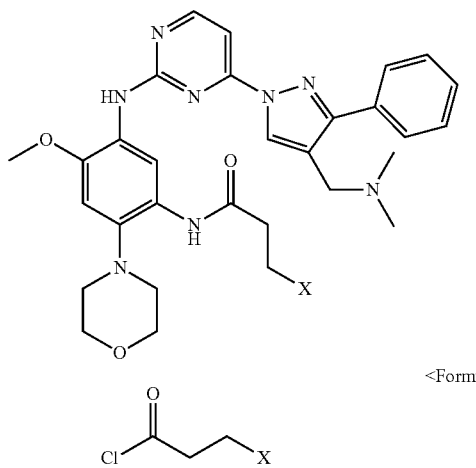

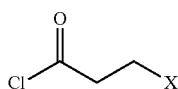

wherein, X is halogen.

2. The process according to claim 1, wherein the reacting of Step (a) is carried out in the presence of one or more base(s) selected from the group consisting of potassium tert-butoxide, sodium hydroxide, potassium hydroxide, lithium hydroxide, sodium hydride, sodium carbonate, sodium bicarbonate, potassium carbonate, potassium phosphate, sodium phosphate, 1,8-diazabicyclo[50.4.0]undec-7-ene, 1,4-diazabicyclo[2.2.2]octane, 1,5-diazabicyclo[4.3.0]non-5-ene, pyridine, triethylamine, diisopropylamine and diisopropylethylamine.

3. The process according to claim 1, wherein the reacting of Step (a) is carried out in the presence of a solvent selected from the group consisting of acetonitrile, methyl ethyl ketone, acetone, methyl isobutyl ketone, dichloromethane, dichloroethane, dimethylformamide, dimethylacetamide, dimethyl sulfoxide, tetrahydrofuran, $C_1 \sim C_5$ alcohol, toluene, ethyl acetate, isopropyl acetate, diethyl ether, water and a mixture thereof.

4. The process according to claim 3, wherein the solvent is selected from the group consisting of acetonitrile, tetrahydrofuran, methyl ethyl ketone, acetone, dichloromethane, water and a mixture thereof.

5. The process according to claim 1, wherein the base used in Step (b) is one or more selected from the group consisting of potassium tert-butoxide, sodium hydroxide, potassium hydroxide, lithium hydroxide, sodium hydride, sodium carbonate, sodium bicarbonate, potassium carbonate, potassium phosphate, sodium phosphate, 1,8-diazabicyclo[5.4.0]undec-7-ene, 1,4-diazabicyclo[2.2.2]octane, 1,5-diazabicyclo[4.3.0]non-5-ene, pyridine, triethylamine, diisopropylamine and diisopropylethylamine.

6. The process according to claim 5, wherein the base is one or more selected from the group consisting of sodium hydroxide, triethylamine and diisopropylamine.

7. The process according to claim 1, wherein the reacting of Step (b) is carried out in the presence of a solvent selected from the group consisting of acetonitrile, methyl ethyl ketone, acetone, methyl isobutyl ketone, dichloromethane, dichloroethane, dimethylformamide, dimethylacetamide, dimethyl sulfoxide, tetrahydrofuran, $C_1 \sim C_5$ alcohol, toluene, ethyl acetate, isopropyl acetate, diethyl ether, water and a mixture thereof.

8. The process according to claim 7, wherein the solvent is selected from the group consisting of acetonitrile, tetrahydrofuran, methyl ethyl ketone, acetone, dichloromethane, water and a mixture thereof.

9. The process according to claim 1, wherein Step (a) and Step (b) are carried out in a one-pot reaction.

10. The process according to claim 1, wherein the N1-(4-(4-((dimethylamino)methyl)-3-phenyl-1H-pyrazol-1-yl)pyrimidin-2-yl)-6-methoxy-4-morpholinobenzene-1,3-diamine in Step (a) is obtained by a process comprising
  (i) reacting 4-(4-((dimethylamino)methyl)-3-phenyl-1H-pyrazol-1-yl)-N-(2-methoxy-4-morpholino-5-nitrophenyl)pyrimidin-2-amine with tin chloride in the presence of hydrochloric acid to obtain a complex of Formula 5 and
  (ii) reacting the complex of Formula 5 with a base to obtain N1-(4-(4-((dimethylamino)methyl)-3-phenyl-1H-pyrazol-1-yl)pyrimidin-2-yl)-6-methoxy-4-morpholinobenzene-1,3-diamine:

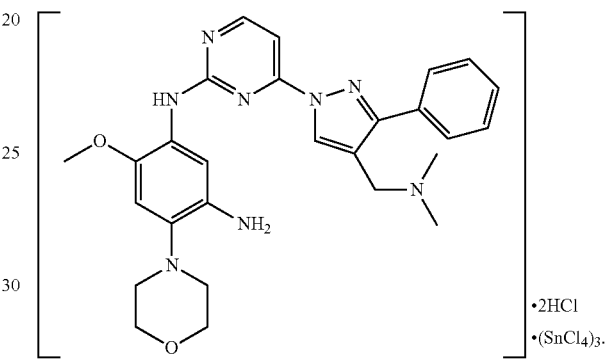

11. The process according to claim 10, wherein the reacting of Step (i) is carried out in the presence of one or more solvent(s) selected from the group consisting of water, $C_1 \sim C_{10}$ alcohol, dichloromethane, tetrahydrofuran, acetonitrile and ethyl acetate.

12. The process according to claim 10, wherein the base used in Step (ii) is one or more selected from the group consisting of sodium hydroxide, potassium hydroxide, sodium carbonate, sodium bicarbonate, potassium carbonate, potassium phosphate, and sodium phosphate.

13. The process according to claim 10, wherein the 4-(4-((dimethylamino)methyl)-3-phenyl-1H-pyrazol-1-yl)-N-(2-methoxy-4-morpholino-5-nitrophenyl)pyrimidin-2-amine is obtained by reacting 1-(2-((2-methoxy-4-morpholino-5-nitrophenyl)amino)pyrimidin-4-yl)-3-phenyl-1H-pyrazole-4-carbaldehyde with dimethylamine or a salt thereof.

14. The process according to claim 13, wherein the reacting is carried out in the presence of one or more reducing agent(s) selected from the group consisting of sodium triacetoxyborohydride, sodium cyanoborohydride and sodium borohydride.

15. The process according to claim 13, wherein the 1-(2-((2-methoxy-4-morpholino-5-nitrophenyl)amino)pyrimidin-4-yl)-3-phenyl-1H-pyrazole-4-carbaldehyde is obtained by reacting 4-chloro-N-(2-methoxy-4-morpholino-5-nitrophenyl)pyrimidin-2-amine with 3-phenyl-1H-pyrazole-4-carbaldehyde.

16. The process according to claim 15, wherein the 4-chloro-N-(2-methoxy-4-morpholino-5-nitrophenyl)pyrimidin-2-amine is obtained by reacting N-(2-methoxy-4-morpholino-5-nitrophenyl)formamide with 4-chloro-2-(methylsulfonyl)pyrimidine.

17. The process according to claim 16, wherein the N-(2-methoxy-4-morpholino-5-nitrophenyl)formamide is obtained by performing a formylation of 2-methoxy-4-morpholino-5-nitroaniline.

18. The process according to claim 17, wherein the formylation is carried out with a mixture of acetic acid and formic acid.

19. The process according to claim 16, wherein the 4-chloro-2-(methylsulfonyl)pyrimidine is obtained by performing an oxidation of 4-chloro-2-(methylthio)pyrimidine.

20. The process according to claim 19, wherein the oxidation is carried out with one or more oxidizing agent(s) selected from the group consisting of potassium permanganate, chromic acid, oxygen, hydrogen peroxide and 3-chloroperbenzoic acid.

21. The process according to claim 13, wherein the 1-(2-((2-methoxy-4-morpholino-5-nitrophenyl)amino)pyrimidin-4-yl)-3-phenyl-1H-pyrazole-4-carbaldehyde is obtained by reacting N-(2-methoxy-4-morpholino-5-nitrophenyl)formamide with 1-(2-(methylsulfonyl)pyrimidin-4-yl)-3-phenyl-1H-pyrazole-4-carbaldehyde.

22. The process according to claim 21, wherein the reacting is carried out in the presence of one or more base(s) selected from the group consisting of sodium $C_1$~$C_6$ alkoxide, potassium $C_1$~$C_6$ alkoxide, sodium carbonate, potassium carbonate, and potassium phosphate.

23. The process according to claim 21, wherein the reacting is carried out in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone.

24. The process according to claim 21, wherein the 1-(2-(methylsulfonyl)pyrimidin-4-yl)-3-phenyl-1H-pyrazole-4-carbaldehyde is obtained by reacting 1-(2-(methylthio)pyrimidin-4-yl)-3-phenyl-1H-pyrazole-4-carbaldehyde with an oxidizing agent.

25. The process according to claim 24, wherein the oxidizing agent is one or more selected from the group consisting of potassium permanganate, chromic acid, oxygen, hydrogen peroxide and 3-chloroperbenzoic acid.

26. The process according to claim 24, wherein the reacting is carried out in the presence of one or more solvent(s) selected from the group consisting of $C_1$~$C_5$ alcohol, carbon tetrachloride, chloroform, dichloromethane, acetone, methyl ethyl ketone, methyl isobutyl ketone, cyclohexanone, pentane, hexane, heptane, octane, nonane, decane, undecane, dodecane, cyclohexane, petroleum ether, kerosene, toluene, xylene, mesitylene and benzene.

27. The process according to claim 24, wherein the 1-(2-(methylthio)pyrimidin-4-yl)-3-phenyl-1H-pyrazole-4-carbaldehyde is obtained by reacting 4-chloro-2-(methylthio)pyrimidine with 3-phenyl-1H-pyrazole-4-carbaldehyde.

28. The process according to claim 27, wherein the reacting is carried out in the presence of one or more base(s) selected from the group consisting of potassium tert-butoxide, sodium hydroxide, potassium hydroxide, sodium hydride, sodium carbonate, potassium carbonate, potassium phosphate, sodium phosphate, 1,8-diazabicyclo[5.4.0]undec-7-ene, 1,4-diazabicyclo[2.2.2]octane, 1,5-diazabicyclo[4.3.0]non-5-ene, pyridine, triethylamine, diisopropylamine and diisopropylethylamine.

29. The process according to claim 27, wherein the reacting is carried out in the presence of one or more solvent(s) selected from the group consisting of dichloromethane, dichloroethane, dimethylformamide, dimethylacetamide, dimethyl sulfoxide, tetrahydrofuran, $C_1$~$C_5$ alcohol, ethyl acetate, acetone, methyl ethyl ketone, acetonitrile and toluene.

30. A compound of Formula 2 or salt thereof:

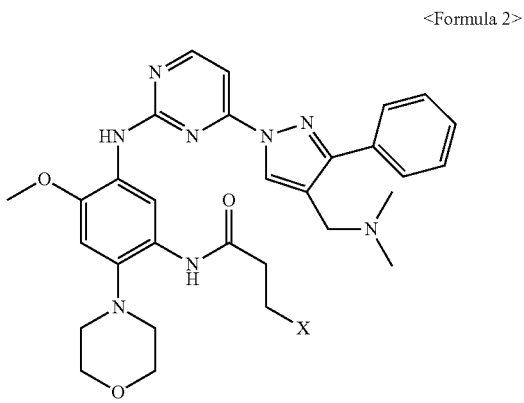

<Formula 2> wherein, X is halogen.

31. A complex of Formula 5:

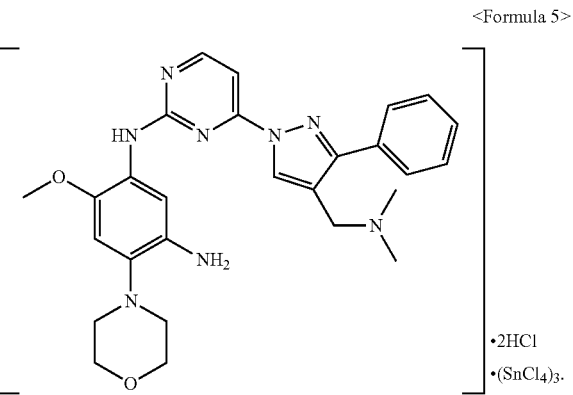

<Formula 5>

·2HCl
·(SnCl$_4$)$_3$.

32. A compound, wherein said compound is 1-(2-(methylsulfonyl)pyrimidin-4-yl)-3-phenyl-1H-pyrazole-4-carbaldehyde.

33. A compound, wherein said compound is 1-(2-(methylthio)pyrimidin-4-yl)-3-phenyl-1H-pyrazole-4-carbaldehyde.

* * * * *